United States Patent [19]

Jackson

[11] Patent Number: 4,623,335
[45] Date of Patent: Nov. 18, 1986

[54] APPARATUS AND METHODS FOR DETECTING PROBE PENETRATION OF HUMAN INTERNAL TARGET TISSUE HAVING PREDETERMINED INTERNAL PRESSURE

[76] Inventor: Anthony Jackson, 13 Cayuse La., Rancho Palos Verdes, Calif. 90274

[21] Appl. No.: 785,923

[22] Filed: Oct. 9, 1985

[51] Int. Cl.⁴ ............................................. A61M 5/00
[52] U.S. Cl. ..................................... 604/118; 128/748
[58] Field of Search ............................... 604/118, 117; 128/673–675, 748

[56] References Cited

U.S. PATENT DOCUMENTS

| | | | |
|---|---|---|---|
| 2,866,453 | 12/1958 | Jewett | 128/674 |
| 3,062,202 | 11/1962 | Ayman et al. | 128/674 |
| 3,183,722 | 5/1965 | Unger et al. | 128/673 X |
| 3,581,733 | 6/1971 | Grandjean | 128/673 |
| 3,610,228 | 10/1971 | Temkin | 128/673 X |
| 3,720,201 | 3/1973 | Ramsey, III | 128/673 |
| 3,730,168 | 5/1973 | McWhorter | 128/748 |
| 3,807,389 | 4/1974 | Miller et al. | 128/674 |
| 3,863,504 | 2/1975 | Borsanyi | 128/673 X |
| 3,920,002 | 11/1975 | Dye et al. | 604/118 X |
| 3,934,576 | 1/1976 | Danielsson | 604/118 X |
| 4,192,319 | 3/1980 | Hargens et al. | 128/673 X |
| 4,217,911 | 8/1980 | Layton | 604/118 X |
| 4,252,126 | 2/1981 | Mandl | 128/673 |
| 4,300,572 | 11/1981 | Knighton | 128/673 X |
| 4,535,773 | 8/1985 | Yoon | 604/118 X |

Primary Examiner—Stephen C. Pellegrino

[57] ABSTRACT

A method for detecting probe penetration of human target tissue having predetermined internal pressure includes inserting a hollow probe into the human body towards the internal target tissue and gradually increasing pressure in a closed volume defined by the probe interior and a conduit communicating therewith until a moveable piston slideably resident within the conduit and having a passageway therethrough connecting the portion of the conduit interior communicating with the hollow probe with an orifice in a lateral surface of the moveable piston slideably contacting said conduit interior, moving in response to pressure within the conduit opposing predetermined bias force applied to the moveable piston, reaches a predetermined position, at which the lateral surface orifice of the moveable piston communicates with ambient air via a passageway through the wall of the conduit, corresponding to pressure in the closed volume equaling the predetermined internal pressure.

Apparatus for detecting probe penetration of human target tissue having predetermined internal pressure includes: an elongated hollow probe, a valve having first and second orifices with the first orifice communicating with the hollow probe, a conduit communicating with the second orifice of the valve, a piston movable resident within the conduit in response to conduit pressure, for limiting pressure within the conduit to the predetermined internal pressure and providing visible indication upon pressure within the conduit reaching the predetermined internal pressure and has a hand squeezable bulb communicating with the conduit intermediate the movable piston and the valve, for increasing pressure within the conduit and the probe until the movable piston limits pressure within the conduit to the predetermined pressure.

21 Claims, 4 Drawing Figures

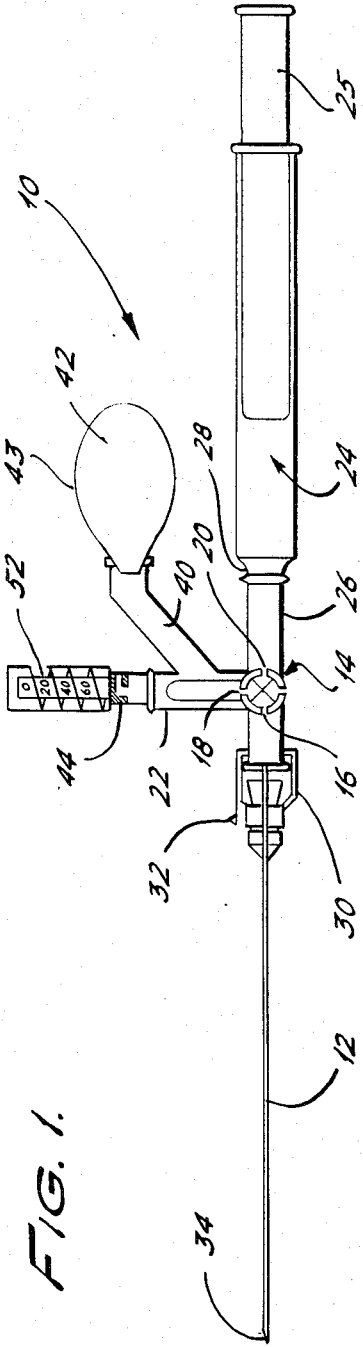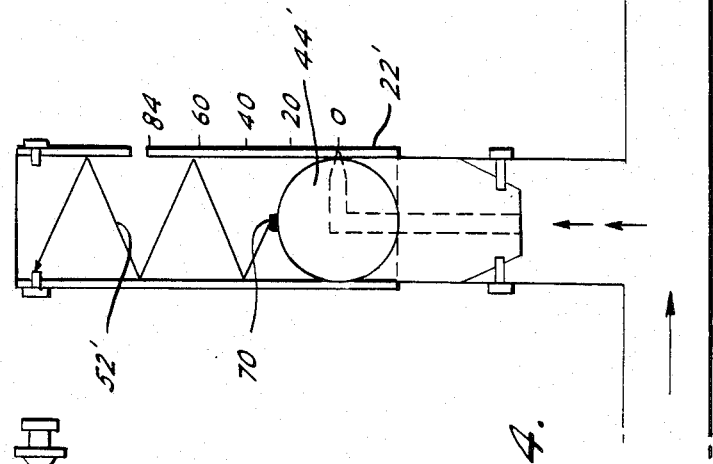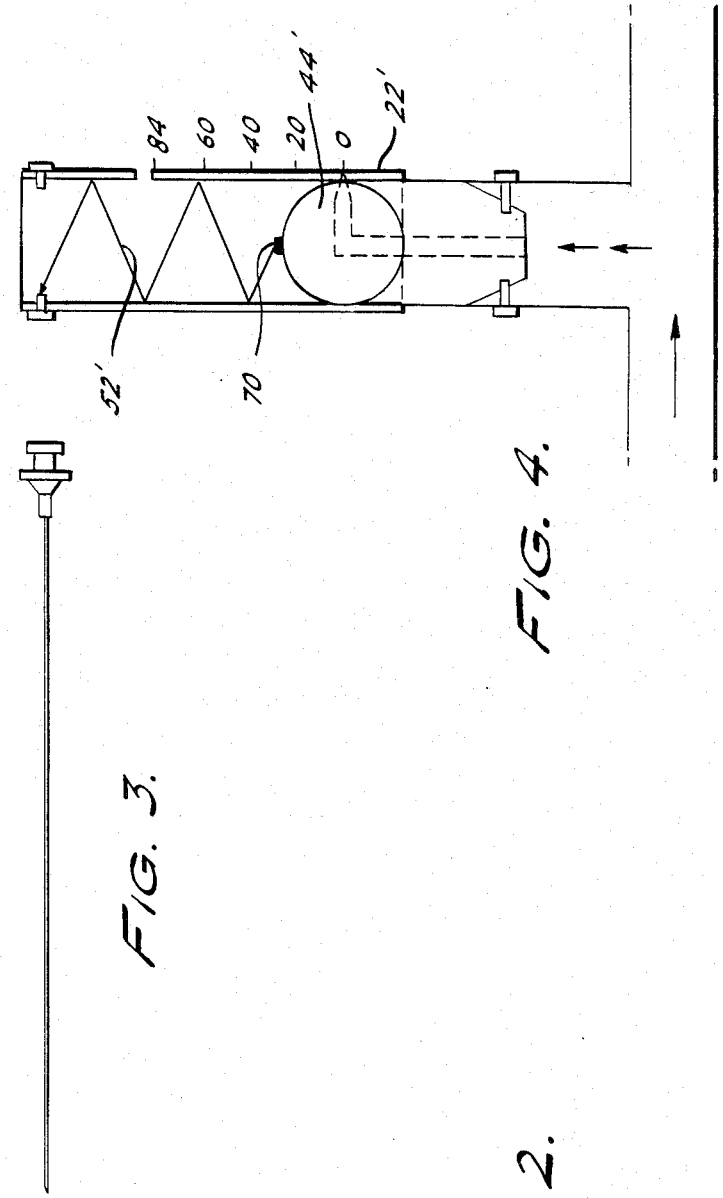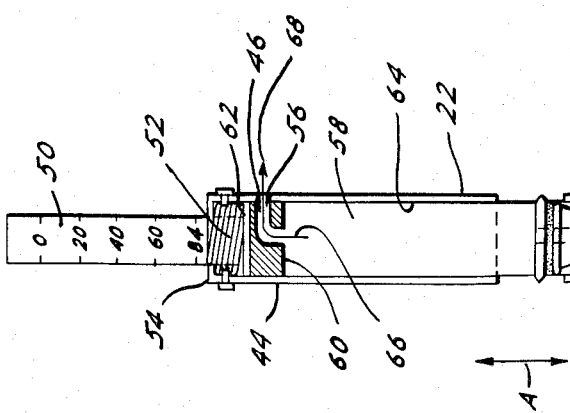

APPARATUS AND METHODS FOR DETECTING PROBE PENETRATION OF HUMAN INTERNAL TARGET TISSUE HAVING PREDETERMINED INTERNAL PRESSURE

FIELD OF THE INVENTION

This invention relates to methods and apparatus for detecting probe penetration into human internal target tissue having a predetermined internal pressure and to introduction of therapeutic substances close to or into the target tissue.

BACKGROUND OF THE INVENTION

In the human body the epidural space is a narrow but important anatomical space or void, filled with areola-type tissue, located in and traversing most of the length of the spine. The epidural space exhibits an internal pressure which research has determined to be at or below atmospheric pressure, customarily measured in units of centimeters of water. The epidural space is important because the epidural space may be used to introduce certain pharmaceutical agents at various positions along the spine. By introduction of anesthetics and/or medication into the epidural space at an appropriate position, a variety of pain causing maladies that afflict the body from head to toe may be treated. Also, the epidural space may be used for injection of local anesthetics to provide regional anesthesia required for various types of surgery. This is especially important when general anesthesia may be contraindicated due to a patient's condition or the particular surgery to be performed.

The epidural space is exceedingly narrow, is close to the spinal cord and, accordingly, accurate identification of the epidural space is exceedingly important. Unfortunately, because of the small size of the epidural space, it is often difficult to locate by even the most skilled physician.

One benchmark for locating the epidural space is the ligamentum-flavum. The ligamentum-flavum is a ligament having unique pressure characteristics which distinguish it from all other anatomical structures in the posterior spine. The ligamentum-flavum is useful in identifying and locating the epidural space because once the ligamentum-flavum is identified, the epidural space is easily identified - the epidural space lies only a few fractions of a centimeter anterior to the ligamentum-flavum.

As is well-known according to various anatomy handbooks, such as *Gray's Anatomy*, the spine has four major divisions—cervical, thorascic, lumbar and sacral. When probing the posterior back at a level below a spinous process, the major anatomical structures encountered when proceeding from dorsal to ventral are the skin, the supraspinous ligament, the intraspinous ligament, the ligamentum-flavum, the epidural space, the dura, the sub-arachnoid space containing spinal fluid and, finally, the spinal cord.

The main body of the spinal cord ends at about the beginning of the lumbar portion of the spine, around the vertebrae generally identified $L_1$-$L_2$. Below this point the spinal cord divides into numerous small filaments, known as the tail of the horse or cauda-equina. The majority of epidural injections are performed at levels below lumbar vertebrae $L_2$, to avoid the devastating consequences of an accidental spinal cord penetration. Because of this danger, many physicians and other clinicians shy away from performing upper level or cervical-thoracic epidural injections because confirmation of correct placement of the injecting needle in the epidural space is often difficult if not impossible using apparatus and methods known heretofore.

The ligamentum-flavum consists of very dense fibernous-membranous tissue, in contrast to the more spongia-type of tissue prevalent in other posterior spinal structures. Because of its unique composition and characteristics, the ligamentum-flavum (which may be the "benchmark" referred to hereinafter) is the only anatomical area in the posterior spine which resists externally applied positive pressure. In other words, air or fluid may be applied externally, against the ligamentum-flavum under a certain amount of positive pressure, whereupon the air or gas is resisted by this ligament, which does not readily transmit, permit diffusion of or propagate such air or gas pressure, in normal, healthy adult patients. In some patients the ligamentum-flavum is denser than in other patients. In patients with less dense ligamentum-flavums, particularly in elderly people in which the integrity of the ligamentum-flavum tissue may have degraded, the ligamentum-flavum may permit slight diffusion of air or gas applied thereagainst. However, in normal, healthy adults, no such diffusion will occur at any conventional gas pressure used for therapeutic application. The ligamentum-flavum makes up the bulk of the posterior border of the epidural space (which may be the "target tissue" referred to hereinafter).

DESCRIPTION OF THE PRIOR ART

Prior art known to applicant includes U.S. Pat. Nos. 2,866,453; 3,062,202; 3,183,722; 3,610,228; 3,720,201; 3,730,168; 3,807,389; 4,192,319; 4,217,911 and 4,252,126. Of these '453 and '722 are believed to be the most relevant with respect to the invention disclosed and claimed herein.

'453 discloses a hypodermic syringe combined with a standard three-way stop cock communicating with a pressure sensitive diaphragm attached to a calibrated manometer. Upon harvesting a particular bodily fluid, such as blood or acetic fluid, with the hypodermic syringe, the fluid may be isolated by the stop cock in the diaphragm-manometer portion of the device, whereupon pressure measurements may be made and recorded.

'722 includes a transparent cylinder having pressure scale markings in centimeters or inches of either water or mercury, in which a spring and a gas-tight movable rod-piston assembly are provided. A hypodermic needle is used via which bodily fluids are shunted first through a transparent channeled nozzle and then into a transparent cylinder. Compression of air in the cylinder is achieved by manually downwardly displacing the piston rod until pressure of liquid exiting the body equals pressure of the air being compressed by the piston within the cylinder. Once equilibrium is attained, pressure is read directly on the scale, using the piston position as the pressure indicator. The spring plays no active role in compression, serving only to return the piston back to its initial position once the measurement has been taken.

While these patents illustrate some development of the body pressure measurement art, none of the devices disclosed are believed useful for locating the epidural space or the ligamentum-flavum. In fact these devices are believed to be of essentially no use in trying to locate the epidural space or the ligamentum-flavum because in locating the epidural space by locating the ligamentum-flavum, internal pressure measurement per se is not so important but generation and measurement of an internal pressure gradient is of critical importance. The need is for generation, delivery and sustenance of an idealized pressure of about eighty-four centimeters of water at the hypodermic needle tip. Research has established eighty-four centimeters of water as an ideal, expected equilibrium pressure within the ligamentum-flavum, as contrasted to the zero or negative gauge pressure within the epidural space.

SUMMARY OF THE INVENTION

This invention encompasses methods and apparatus for detecting probe penetration of human internal target tissue having predetermined internal pressure characteristics. Apparatus embodying aspects of the invention includes an elongated hollow probe, a valve having first and second orifices, with means for optionally connecting said orifices together with the first orifice being connected to the hollow probe. A conduit is connected to the second orifice of the valve. Within the conduit there is moveable means for limiting pressure, within the portion of the conduit connected to the hollow interior of the probe, to a predetermed internal pressure and providing visible indication that the predetermined internal pressure has been reached within the conduit.

The apparatus further includes means communicating with the conduit, at a position intermediate the moveable means and the valve means, for increasing pressure within the conduit and the probe until the moveable means limits pressure within the conduit to the predetermined amount. The apparatus may further include biasing means for resisting movement of the moveable means in response to pressure build-up in the conduit due to the pressure increasing means increasing conduit internal pressure. The moveable means preferably has a passageway therethrough connecting a surface portion of the moveable means which receives pressure in the conduit with the surface portion of the moveable means which slideably contacts the conduit inner wall. The conduit wall has an orifice therethrough for communicating with the passageway at the slideably contacting surface portion of the moveable means when the moveable means has moved the slideably contacting surface portion thereof into communication therewith, in response to pressure build-up in the conduit due to operation of the pressure increasing means.

The invention further encompasses methods for detecting probe penetration of human internal target tissue, such as the benchmark ligamentum-flavum, having predetermined internal pressure characteristics, by inserting a hollow probe into the human body towards the internal target tissue. Pressure in an essentially closed volume defined by a probe hollow interior and a conduit communicating with the probe is increased until a moveable member, having a passageway therethrough connecting the portion of the conduit which communicates with the hollow probe interior with an orifice formed in a moveable member lateral surface, reaches a position, in opposition to predetermined bias force applied to the moveable member, at which a passageway orifice formed in the lateral surface of the moveable member communicates with ambient air through the passageway in the wall of the conduit, thereby limiting internal pressure in the passageway to the predetermined internal pressure of the target tissue.

A BRIEF DESCRIPTION OF THE DRAWINGS

FIG. 1 is a partially sectioned side elevation of apparatus embodying aspects of the invention.

FIG. 2 is a partially broken, partially sectional enlarged view of a portion of the apparatus shown in FIG. 1.

FIG. 3 is a side view of a stylet insertable into a portion of the apparatus shown in FIG. 1.

FIG. 4 is a partially broken side elevation of an alternate embodiment of the portion of the apparatus illustrated in FIG. 2.

DESCRIPTION OF THE PREFERRED EMBODIMENTS AND BEST MODE FOR PRACTICING THE INVENTION

Referring to the drawings in general and to FIG. 1 in particular, apparatus for detecting probe penetration of human internal target tissue and, optionally, injecting thereinto a therapeutically desired pharmaceutical substance is designated generally 10 and includes an axially elongated hollow needle-probe 12, a valve member, depicted schematically as 14 in FIG. 1, having first, second and third orifices designated 16, 18 and 20 respectively and including a rotatable central member, not shown, for optionally connecting any two or all three of orifices 16, 18, 20 together. Valve 14 is preferably a rotatable, conventional three-way stop cock valve, well-known in the art.

First orifice 16 is connected to and communicates with a hollow interior of needle-probe 12. Second orifice 18 is connected to and communicates with a hollow interior of a conduit 22 extending away from valve 14 as illustrated in FIG. 1. Third orifice 20 of valve 14 is connected to and communicates with means 24 for pumping medication into the hollow interior of needle-probe 12 through valve 14 via first and third orifices 16 and 20. Means 24 is preferably provided by a conventional thumb-powered syringe which may be removeably detached from valve member 14 and communicates therewith via a conduit 26. Connection means 28 between medication pumping means 24 and third conduit 26 is conventional.

Needle-probe 12 is preferably a standard number seventeen gauge Tuey puncture needle. Probe 12 fits within a collar 30 disposed about an extended portion of third conduit 26. Valve 14 resides centrally with respect to third conduit 26. Third conduit 26 extends on either side of valve 14 to provide suitable orifices for communication of needle-probe 12 and medication pumping means 24 with valve 14. The first, second and third orifices of valve 14, namely orifices 16, 18 and 20 respectively, are within the housing for valve 14 defined generally by third conduit 26.

Collar 30 is rotatable to release needle-probe 12 from the extended portion of third conduit 26. Affixed to collar 30 is a pointer 32 located at a position so that the tip of pointer 32 always corresponds to the direction of the beveled tip 34 of the Tuey needle. Note that in FIG. 1 both pointer 32 and the bevel of tip 34 of the Tuey needle are in the plane of the paper.

The coupling provided by collar 30 between a base 36 of needle-probe 12 and the end 38 of third conduit 26 is conventional.

As illustrated in FIG. 1, needle-probe 12 and medication pumping means 24 preferably lie along an axis of alignment with third conduit 26 and valve member 14. Of course, medication pumping means 24 can be disconnected from conduit 26 at juncture 28 and an appropriate stylet, such as shown in FIG. 3, may be inserted at juncture 28 through conduit 26 and through the interior of hollow needle-probe 12 to extend to needle tip 34.

Conduit 22 preferably extends transversely away from the axis of conduit 26, as illustrated in FIG. 1. Communicating with first conduit 22, preferably at a position slightly removed from juncture of first conduit 22 with second orifice 18, is a second conduit 40. Second conduit 40 preferably extends away from first conduit 22 at an angle of about 45° and, accordingly, second conduit 40 preferably makes an angle of about 45° with the axis of alignment of third conduit 26, probe 12, medication pumping means 24, and the like. At an end of second conduit 40 remote from the point of communication between first conduit 22 and second conduit 40 is a hand squeezable bulb 42 providing means for increasing pressure within conduits 22 and 40, and also within hollow probe 12 when valve member 14 is positioned for communication between the hollow interior of needle-probe 12 and the interior of conduit 22.

Slideably resident within conduit 22 is a moveable piston 44 including a passageway 46 therethrough; this structure is best shown in FIG. 2. A resilient coil spring 52 applies bias to moveable piston 44 in opposition to internal pressure within conduit 22, acting against piston 44. Spring 52 may reside within conduit 22, between moveable piston 44 and a cap member 54 which closes the end of conduit 22 remote from valve 14.

Referring to FIG. 2, conduit 22 includes an orifice 56 formed in the side wall thereof, providing communication between the hollow interior 58 of conduit 22 and ambient atmosphere. Moveable piston 44 has a bottom surface 60 receiving internal pressure within conduit 22. Pressure within conduit 22 acting against the area of piston bottom surface 60 produces a force directed upwardly in FIG. 2, tending to move piston 44 upwardly within conduit 22 against bias provided by spring 52.

Piston 44 has a lateral side surface 62 slideably contacting interior surface 64 of conduit 22. Passageway 46 through piston 44 terminates at respective orifices 66, 68 formed respectively in bottom surface 60 and lateral surface 62 of piston 44. While piston 44 may move reciprocably within conduit 22 in the direction indicated by arrow A in FIG. 2, piston 44 is precluded from rotating within conduit 22 about the axis thereof. Any suitable means may be used to preclude such rotation; for example, piston 44 and the interior of conduit 22 may be configured with square cross-section or piston 44 and conduit 22 may have round cross-section but may be provided with a track or runner axially extending within conduit 22 to prevent rotation of piston 44. In the embodiment illustrated in FIGS. 1 and 2, the rectangular cross-section of rod 50 fitting slidably within a corresponding rectangular clearance passageway of cap 54 prevents such rotation because rod 50 is affixed to piston 44. Of course, lateral side surface 62 and conduit internal surface 64 mate closely so liquid or air under pressure cannot escape from the conduit interior between the piston and the conduit wall.

Piston 44 is not permitted rotate within conduit 22, in order to assure that as piston 44 rises to the position illustrated in FIG. 2, orifice 68 formed in lateral surface 62 of piston 44 communicates with orifice 56 formed in sidewall of conduit 22. At the position shown in FIG. 2, pressure within conduit 22 is relieved to atmosphere as gas or liquid within conduit 22 escapes to atmosphere via passageway 46.

Spring 52 is selected to have a spring constant and is positioned so that piston 44 will reach the position at which orifice 68 communicates with orifice 56 when pressure within conduit 22 equals a preselected pressure corresponding to internal pressure of a selected human organ; dimensions of the apparatus are correspondingly selected according to the desired preselected pressure. For example, if the apparatus is to be used to detect penetration of the ligamentum-flavum by the needle-probe tip, spring 52 and the position of orifice 56 are selected so that the preselected pressure, at which passageway 46 communicates with orifice 56, is eighty-four centimeters of water.

When the predetermined pressure is reached within conduit 22, piston pressure is relieved via escape of gas through passageway 46 and orifice 68. Once the pressure is slightly relieved, bias applied by spring 52 forces piston 44 downwardly as viewed in FIG. 2, thereby interrupting communication between passageway 46 and orifice 68, once again sealing the interior of conduit 22 against escape of pressurized liquid or gas therefrom.

Referring once again to FIG. 1, conduit 40 and hand squeezable bulb 42 are preferably coplanar with needle-probe 12, valve 14 and medication pumping means 24, as illustrated in FIG. 1. The angular configuration of the portion of conduit 40 communicating with conduit 22, coupled with the bend in conduit 40 so that the portion of conduit 40 with which bulb 42 communicates is essentially parallel with the axis of alignment of probe 12, valve 14 and medication pumping means 24, permits comfortable hand positioning by the operator of the apparatus.

Typically, a physician may grasp the apparatus by gripping conduit 26 with the first two fingers of his left hand and applying his thumb to piston 25 to inject a therapeutically desired pharmaceutical substance into the patient. With the apparatus thus held by his left hand, the physician can use his right hand to pump squeeze bulb 42 thereby to increase pressure within conduit 22, and within the hollow interior of probe 12 if valve 14 is positioned for communication therebetween.

In one preferred embodiment of the invention hand squeezable bulb 42 supplies a constant volume of three cubic centimeters of air each time the bulb is substantially completely squeezed. The bulb 42 preferably includes a dorsal opening conveniently positioned to be covered by the operator's thumb, with the opening indicated as 43 in FIG. 1. Opening 43, when uncovered by the operator's thumb, permits rapid refill of hand squeezable bulb 42.

The apparatus may be used in practicing a method of the invention for determining location and penetration by probe 12 of a selected internal body organ having a predetermined internal pressure, which may be higher than atmospheric. In one preferred method, the apparatus is used to locate the ligamentum-flavum. From the ligamentum-flavum, the epidural space, which is immediately adjacent to and essentially bounded by the ligamentum-flavum, can be located.

To locate the ligamentum-flavum in the body, the physician, utilizing the apparatus disclosed in FIG. 1, selects a desired position between two vertebrae at which the ligamentum-flavum is to be located. Gripping the apparatus of FIG. 1 with one hand, the physician inserts needle-probe 12 slowly into the body. As the needle is advanced, the physician rapidly presses and refills bulb 42, thereby sending forth in rapid succession constant volume bursts of air, preferably three cubic centimenters each, that effectively bombard the tissues encountered by the needle tip 34 as it approaches the ligamentum-flavum. While doing this the physician watches scale 48, as pressure indicating indicia rod 50 extending from piston 44 rises unitarily with piston 44, as piston 44 moves upwardly within conduit 22. The physician continues to squeeze bulb 42, thereby continuing to inject air into the system defined by the interior of conduit 22 and the hollow interior of needle-probe 12. Valve 14 is, of course, positioned so that conduit 22 communicates with hollow interior of needle-probe 12 and medication pumping means 24 is isolated from the remainder of the system.

As pressure within conduit 22 rises and approaches eighty-four centimeters of water, indicating intersection of the tip 34 of the hollow needle-like probe 12 with the boundary of the ligamentum-flavum, orifice 68 in piston 44 approaches orifice 56 in the side wall of conduit 22. Upon tip 34 penetrating the core of the ligamentum-flavum, the system becomes essentially closed, due to the internal pressure characteristics of the ligamentum-flavum. As the pressure reaches eighty-four centimeters of water, orifices 56 and 68 communicate, thereby preventing internal pressure within the system from exceeding eighty-four centimeters of water. Resultant relief of internal pressure permits spring 52 to move piston 44 slightly downwardly within conduit 22, thereby breaking communication between orifices 68 and 56.

When piston 44 moves slightly downwardly within conduit 22, breaking connection between orifices 56 and 68 and re-establishing the "essentialy closed" nature of the system, the attending physician must maintain the bulb in its collapsed state which the bulb had assumed when the system vented to the atmosphere due to the brief communication between orifices 56 and 68. The attending physician accomplishes this by maintaining his thumb in position covering opening 43 of bulb 42. This collapsed state of bulb 42 reduces the internal volume of the re-established essentially closed system, making piston 44 even more responsive to pressure encountered by tip 34 of needle-like probe 12 and independent of other external influences. Note that at this point the attending physician relies only on the visibly signaled pressure as an indication of the location of tip 34 of needle-like probe 12; he does not rely on any tactile sensation.

Due to the re-established "essentially closed" nature of the system, pressure within the system will be maintained at eighty-four centimeters of water, which signifies that needle tip 34 is within the ligamentum-flavum; positive pressure of eighty-four centimeters of water indicates the interior of the ligamentum-flavum. The hand squeezable bulb 42 remains compressed yet pressure within the system, as indicated by indicia 50, remains at eighty-four centimeters of water due to its balance with the internal pressure of the ligamentum-flavum as propagated via needle-probe 12 and conduit 22 to the lower surface of piston 44.

Once the ligamentum-flavum has been sensed and located, advancement of needle probe 12 a few fractions of a centimeter causes tip 34 to penetrate the epidural space. Such penetration is indicated by a sudden downward plunge of calibrated indicia bearing rod 50, from eighty-four centimeters of water to zero centimeters of water, which is indicative of the essentially zero pressure within the epidural space being propagated into the system.

Once this movement of calibrated indicia bearing rod 50 has confirmed entry of needle tip 34 into the epidural space, the epidural space is ready to be injected with appropriate medication or anesthetic. However, before this is done, the needle tip should be manually rotated by turning collar 30 to a position at which pointer 32, and hence bevel tip 34 of needlepont 12, points either directly downwards or upwards, assuming the patient is lying on his or her side, in a direction transverse to the axis of the patient's spinal cord. This insures proper spread of the injectate, either downwards or upwards, within the epidural space, thereby effectively limiting the injectate to a given location along the length of the spinal column. If this is not done, parallel spread or flow of the injectate may result, with inferior or undesired therapeutic results.

FIG. 4 illustrates another embodiment of the apparatus in which piston 44' has a spherical shape with bias member 52' secured to the upper extremity of piston 44' may be a metal or plastic ball assembly; of course, the size of piston 44' is selected so that a liquid and gas-tight seal is achieved between piston 44' and the interior wall of second conduit 22'. As illustrated, there may be a support member 100 in the seal conduit 22 for supporting piston 44 and limiting downward travel thereof. The support member is appertured, as shown by dotted lines, to provide fluid communication between the lower section of piston 44' and the portion of conduit 22 most proximate the valve which, of course, has not been illustrated in FIG. 4.

In the embodiment illustrated in FIG. 4, pressure indicating indicia appear on the side wall of second conduit 22' since the piston rod has been eliminated. Preferably the wall of conduit 22' is transparent so that the operator of the apparatus can observe movement of piston 44' upwardly and downwardly within conduit 22' and thereby determine the internal pressure within the system based on where piston 44' is along the scale of pressure indicating indicia. Functional equivalents of other parts illustrated in FIG. 4 corresponding to those illustrated in FIG. 2 have not been numbered in FIG. 4, to assure drawing clariry.

In yet another embodiment of apparatus of the invention, passageway 46 is omitted from piston 44 and orifice 56 is omitted from the side wall of conduit 22. When the apparatus of FIG. 1 is so-modified, the necessary pressure gradient for detecting penetration of the ligamentum-flavum by needle tip 34 may still be determined by observing pressure via movement of rod 50. However, independent maintenance of system internal pressure equal to internal pressure of the ligamentum-flavum cannot be verified using this modified embodiment of the apparatus.

I claim the following:

1. Apparatus for detecting probe penetration of human internal target tissue and injecting a therapeutically desired substance into a selected area proximate said target tissue, comprising:
   a. an axially elongated hollow needle-like probe;
   b. a valve member having first, second and third orifices and including means for optionally connecting any two or all three of said orifices together, said first orifice being connected to said probe hollow interior;

c. means for pumping medication into said probe interior through said valve member via said third orifice;
d. a conduit connected to said second orifice of said valve member;
e. moveable means slideably resident within said conduit and including passage means connecting a first conduit interior portion which is between said moveable means and said valve with an orifice formed in a lateral surface of said movable means which slideably contacts said conquit wall, for limiting pressure within said conduit and said probe to said predetermined internal pressure and providing visible indication that said predetermined internal pressure has been reached within said first conduit and said probe;
f. said conduit having an orifice in the wall thereof for communication of said moveable means lateral surface orifice with ambient atmosphere exterior said conduit;
g. means communicating with said conduit intermediate said movable means and said valve, for increasing pressure within said conduit until said moveable means lateral surface orifice communicates with said passageway formed in the wall of said conduit.

2. Apparatus of claim 1 further comprising means for biasing said moveable means in opposition to pressure in said conduit between said moveable means and said valve.

3. Apparatus of claim 2 wherein said probe is a hypodermic needle, said valve is a three-way rotatable valve, said means for medication pumping is a translucent syringe and said syringe and said probe are axially aligned.

4. Apparatus of claim 3 wherein said conduit extends generally transversely to said alignment axis of said probe and said syringe.

5. Apparatus of claim 4 wherein said conduit has a closed end remote said valve member.

6. Apparatus of claim 4 wherein said biasing means is a compressible spring.

7. Apparatus of claim 6 further comprising pressure indicating indicia associated with said moveable member for indicating pressure within said conduit as said member moves against said spring bias.

8. Apparatus of claim 7 wherein said pressure increasing means is means for repeatedly injecting a preselected volume of gas into said conduit.

9. Apparatus of claim 8 wherein said gas injecting means is a hand squeezable bulb.

10. Apparatus of claim 9 wherein said hand squeezable bulb is generally coplanar with said conduit, said probe and said syringe.

11. Apparatus of claim 10 wherein said hand squeezable bulb communicates with said conduit via a tubular member having an axis forming an acute angle with said conduit and said alignment axis.

12. A method for detecting probe penetration of human target tissue having predetermined internal pressure and injecting a therapeutically desired substance into selected area proximate said target tissue, comprising:
a. inserting a hollow probe into the human body towards said target tissue;
b. increasing pressure in an essentially closed system defined by said probe hollow interior and a conduit communicating with said probe by forcing gas into said conduit until a moveable member including a passageway therethrough connecting the portion of said conduit connecting said hollow probe interior with an orifice formed in a moveable member lateral surface which slideably contacts said conduit interior, slideably moves within said conduit in opposition to predetermined bias force which varies with movement of said moveable member, reaches a position at which said orifice formed in a lateral surface of said movable member communicates with ambient air through a passageway in the wall of said conduit and at which said predetermined bias force corresponds to said predetermined pressure;
c. moving said probe so that the probe tip moves from said target tissue to said selected area; and
d. injecting said therapeutically desired substance into said selected area.

13. The method of claim 12 wherein increasing the depth of insertion of said probe and injecting gas into an essentially closed system defined by said probe hollow interior and said conduit between said probe and said moveable member are performed simultaneously.

14. The method of claim 13 further comprising applying bias to said moveable member in opposition to pressure acting against said moveable member in said conduit.

15. The method of claim 14 wherein injecting gas is performed by repeatedly squeezing a constant volume hand bulb.

16. The method of claim 15 wherein said gas is air.

17. The method of claim 15 wherein said gas is inert.

18. Apparatus for detecting probe penetration of human target tissue having predetermined internal pressure, comprising:
(a) an elongated hollow probe;
(b) valve means having first and second orifices, said first orifice communicating with said hollow probe;
(c) a conduit communicating with said second orifice of said valve means;
(d) means movably resident within said conduit in response to conduit pressure, for limiting pressure within said conduit to said predetermined internal pressure and providing visible indication upon pressure within said conduit reaching said predetermined internal pressure;
(e) means, communicating with said conduit intermediate said movable means and said valve means, for increasing pressure within said conduit and said probe until said movable means limits pressure within said conduit to said predetermined pressure.

19. Apparatus of claim 18 further comprising biasing means for resisting movement of said movable means in response to pressure buildup in said conduit due to said pressure increasing means.

20. Apparatus of claim 18 wherein said movable means has a passageway therethrough connecting a surface portion of said movable means which receives said pressure in said conduit with a surface portion of said movable means which slideably contacts said conduit and wherein said conduit wall has an orifice therethrough for communicating with said passageway at said slidably contacting surface portion of said movable means when said movable means has moved said slidably contacting surface portion thereof into communication therewith in response to pressure buildup in said conduit due to operation of said pressure increasing means.

21. Apparatus for detecting probe penetration of human target tissue and injecting a therapeutically desired substance into a selected area proximate said target tissue, comprising:
- (a) an axially elongated hollow needle-like probe having a beveled tip opening communicating with said hollow interior;
- (b) a three-way valve member having first, second and third orifices and including means for optionally connecting any two or all three of said orifices together, said valve member being connected to said probe and said first orifice of said valve member communicating with said hollow probe interior;
- (c) means for pumping said therapeutically desire substance into said valve member via said third orifice;
- (d) a first conduit connected to said second orifice of said valve member;
- (e) a piston moveably resident within said first conduit for limiting pressure within said first conduit to said predetermined internal pressure of said human internal target tissue and including an extended portion thereof for indicating pressure within said first conduit by movement of a graduated pressure scale unitarily with movement of said piston;
- (f) biasing spring means for resisting movement of said piston in response to pressure buildup in said first conduit between said moveable piston and said three-way valve;
- (g) said first conduit including a passageway formed in the wall thereof for communication therethrough of an orifice in a lateral surface of said moveable piston with ambient atmosphere outside of said first conduit;
- (h) a second conduit communicating with said first conduit intermediate said moveable piston and said valve;
- (i) hand squeezable bulb means disposed at an end of said second conduit remote from said first conduit, for increasing pressure within said second conduit, said first conduit and said hollow probe interior when said valve is positioned permitting communication between said first conduit and said hollow probe interior to the exclusion of said pumping means, for increasing pressure therewithin until said moveable piston limits pressure within said first conduit to said predetermined pressure level;

wherein said pumping means is axially elongated and generally axially aligned with said probe; wherein said valve member is positionable permitting straight line axial communication between said pumping means and said probe interior;
- (j) axially elongated stylet means removeably resident within said hollow probe and said valve member, passing through said first and third orifices of said valve member and extending axially away from said tip of said probe through said valve member for stylet withdrawal from said probe via said valve member;

wherein said first conduit extends generally transversely to said alignment axis of said probe and said pumping means; wherein said moveable piston has a passageway therethrough connecting a surface portion of said moveable piston which facingly receives pressure in said first conduit with a lateral surface of said moveable piston slideably contacting said first conduit and communicating with said orifice through said first conduit wall upon piston movement in opposition to said biasing spring in response to pressure within said first conduit reaching said predetermined internal pressure;

wherein said second conduit is generally coplanar with said first conduit and said axis of alignment of said probe and said pumping means;

wherein said second conduit extends away from said first conduit at a position removed from said point of communication between said first conduit and said valve member at an angle of about 45° to said axis of elongation; and wherein said second conduit has a portion proximate said end thereof to which said hand bulb is connected, which is aligned with said alignment axis.

* * * * *